US005859068A

United States Patent [19]
Wilson

[11] Patent Number: 5,859,068
[45] Date of Patent: Jan. 12, 1999

[54] ACCELERATION OF TISSUE GROWTH USING FLUOROCARBON LIQUID

[75] Inventor: Jay M. Wilson, Weston, Mass.

[73] Assignee: Children's Medical Center Corporation, Boston, Mass.

[21] Appl. No.: 394,186

[22] Filed: Feb. 24, 1995

[51] Int. Cl.$^6$ ................................................. A61K 31/02
[52] U.S. Cl. ........................ 514/761; 514/743; 514/744; 514/745; 514/747; 514/751; 514/752; 514/753; 514/755; 514/756; 514/759
[58] Field of Search ..................... 514/761, 743, 514/744, 745, 747, 751, 752, 753, 755, 756, 759

[56] References Cited

U.S. PATENT DOCUMENTS 3,975,512  8/1976  Long ........................................... 424/5

OTHER PUBLICATIONS

Artificial Cells, Blood Substitutes, and Immobilization Biotechnology, vol. 22, No. 2, 1994, pp. 315–326, XP000579555, Shaffer, T.H., et al., "Perfluorochemical Liquid as a Respiratory Medium".

Artificial Cells, Blood Substitutes, and Immobilization Biotechnology, 1995, 23/3 (417–422), USA, XP000579310, Lowe, K.C., et al., "Enhanced Protoplast Growth at the Interface Between Oxygenated Fluorocarbon Liquid and Aqueous Culture Medium Supplemented with Pluronic F–68".

Critical Care Medicine, vol. 23, No. 11, Nov. 1995, pp. 1858–1863, XP000579573, Wilcox, et al., "Perfluorocarbon–Associated Gas Exchange Improves Pulmonary Mechanics, Oxygenation, Ventilation, and Allows Nitric Oxide Delivery in the Hypoplastic Lung Congenital Diaphragmatic Hernia Oxide Delivery in the Hypopplastic Lung Congenital Diaphragmatic Hernia Lamb Model".

Journal of Applied Physiology, vol. 72, No. 3, Mar. 1992, pp. 1024–1031, XP000579571, Wolfson, M.R., et al., "Comparison of Gas and Liquid Ventilation: Clinical, Physiological, and Histological Correlates".

Journal of Pediatric Surgery, vol. 30, No. 8, Aug. 1995, pp. 1178–1182, XP000579547, Major, et al. "Combined Gas Ventilation and Perfluorochemical Tracheal Instillation as an Alternative Treatment for Lethal Congenital Diaphragmatic Hernia in Lambs".

Pediatric Research, 37 (4 Part 2), 1994, 220A, XP000579554, Leach, et al., "Partial Liquid Ventilation with Liquivent: A Pilot Safety and Efficacy Study in Premature Newborns with Severe Respiratory Distress Syndrome (RDS)".

Proc Natl Acad Sci USA, 80 (18), 1983, 5622–5626, XP000578347, Keese, et al., "Cell Growth on Liquid Interfaces Role of Surface Active Compounds".

Surgical Forum, vol. 44, 1993, pp. 646–649, XP000579556, Hirschl, et al., "Partial Liquid Ventilation Improves Gas Exchange in the Setting of Respiratory Failure during Extracorporeal Life Support (ECLS)".

Morphological effects of chronic tracheal ligation and drainage in the fetal lamb lung Alcorn, et al., *Journal of Anatomy*, 123: No. 3, pp. 649–660 (1977).

Congenital Diaphragmatic Hernia: Predictors of Severity in the ECMO Era Wilson, et al., *Journal of Pediatric Surgery*, 26: No. 9, pp. 1028–1034 (Sep. 1991).

Delayed Repair and Preoperative ECMO Does Not Improve Survival in High–Risk Congenital Diaphragmatic Hernia Wilson, et al., *Journal of Pediatric Surgery*, 27: No. 3, pp. 368–375 (Mar. 1992).

Pulmonary Growth and Remodeling in Infants With High-Risk Congenital Diaphragmatic Hernia Beals, et al., *Journal of Pediatric Surgery*, 27: No. 8, pp. 997–1002 (Aug. 1992).

Congenital Diaphragmatic Hernia, Stabilization and Repair on ECMO Lally, et al., *Annals of Surgery*, 216: No. 5, pp. 569–573 (Nov. 1992).

Intratracheal Pulmonary Ventilation and Congenital Diaphragmatic Hernia: A Report of Two Cases Wilson, et al., *Journal of Pediatric Surgery*, 28: No. 3, pp. 484–487 (Mar. 1993).

Experimental Fetal Trachael Ligation Prevents the Pulmonary Hypoplasia Associated With Fetal Nephrectomy: Possible Applications for Congenial Diaphragmatic Hernia Wilson, et al., *Journal of Pediatric Surgery*, 28: No. 11, pp. 1433–1440 (Nov. 1993).

Experimental Fetal Trachael Ligation Reverses the Structural and Physiological Effects of Pulmonary Hypoplasia in Congenital Diaphragmatic Hernia DiFiore, et al., *Journal of Pediatric Surgery*, 29: No. 2, pp. 248–257 (Feb. 1994).

Congenital Diaphragmatic Hernia: The Hidden Morbidity Lund, et al., *Journal of Pediatric Surgery*, 29: No. 2, pp. 258–264 (Feb. 1994).

Antenatal Diagnosis of Isolated Congenital Diaphragmatic Hernia Is Not and Indicator of Outcome Wilson, et al., *Journal of Pediatric Surgery*, 29: No. 6, pp. 815–819 (Jun. 1994).

Evolution of the Technique of Congenital Diaphragmatic Hernia Repair on ECMO Wilson, et al., *Journal of Pediatric Surgery*, 29: No. 8, pp. 1109–1112 (Aug. 1994).

Congenital Diaphragmatic Hernia and Associated Anomalies: Their Incidence, Identification, and Impact on Prognosis Fauza, et al., *Journal of Pediatric Surgery*, 29: No. 8, pp. 1113–1117 (Aug. 1994).

Lung Development DiFiore, et al., *Seminars in Pediatric Surgery*, 3: No. 4, pp. 221–232 (Nov. 1994).

Lung liquid, fetal lung growth, and congenital diaphragmatic hernia DiFiore, et al., *Pediatric Surgery Int.*, 10: pp. 2–9 (1995).

Experimental Fetal Tracheal Ligation and Congenital Diaphragmatic Hernia: A Pulmonary Vascular Morphometric Analysis DiFiore, et al., *Journal of Pediatric Surgery*, 30: No. 7, to be published Jul. 1995.

Medline Abstract 95152782 (Hirschl et al, 1994).

Chemical Abstracts 101:105184 (Reich elt, 1984).

*Primary Examiner*—Keith D. MacMillan
*Attorney, Agent, or Firm*—Knobbe, Martens, Olson & Bear, LLP

[57]     ABSTRACT

A method for the acceleration of tissue growth using continuous fluorocarbon liquid-based positive pressure is disclosed, whereby significant increase in tissue growth is achieved.

11 Claims, 2 Drawing Sheets

ACCELERATION OF TISSUE GROWTH USING FLUOROCARBON LIQUID

FIELD OF THE INVENTION

This invention relates to medical procedures in which tissue growth is facilitated by maintaining continuous fluorocarbon liquid-based positive pressure.

BACKGROUND OF THE INVENTION

Pulmonary hypoplasia continues to be the most significant limiting factor for the survival of neonates with congenital diaphragmatic hernia (CDH), renal dysplasia or other conditions associated with lung underdevelopment. Although there is some degree of lung growth and remodeling soon after birth, those changes occur over a period of time that exceeds the current limitations of supportive treatment, which includes mechanical ventilation, high-frequency ventilation, and extracorporeal membrane oxygenation (ECMO). In addition, some studies suggest that mechanical ventilation of the hypoplastic lungs actually contributes to an impairment of subsequent alveolar development. As a result, all patients with severe forms of lung hypoplasia are still unsalvageable.

There is evidence that lung liquid is critical to lung growth in the fetus and that fetal lung liquid volume must be maintained for normal lung growth to occur. It is well known, through several controlled studies as well as experiments of nature, that complete occlusion of the fetal airway markedly accelerates pulmonary growth, sometimes even beyond normal limits, both in otherwise normal and in hypoplastic lungs. Fetal tracheal occlusion, while preserving the normal maturation process, also reverses pulmonary hypoplasia associated with experimental CDH and produces lungs that are more compliant and more efficient at gas exchange.

Although the specific mechanisms responsible for pulmonary growth or hyperplasia after fetal airway occlusion are not known, there is strong evidence that increased intratracheal (ITP) and intrapulmonary (IPP) pressure plays a major role in the process. In normal fetal lambs, maximal lung growth occurs between 112 and 124 days' gestation, a period which coincides with significant elevation in ITP. Animals submitted to fetal tracheal ligation have been found to have ITP of 6–7 mm Hg, well above the 1.8–2.0 mm Hg values reported in normal fetal lambs of similar gestational age in utero. Those findings are in accordance with the observations of Alcorn et al., who reported ITP of 6.4 mm Hg in fetal lambs submitted to tracheal ligation (*J Anat* 123:649–660 (1977)). Conversely, chronic drainage of fetal lung liquid and deceased ITP leads to pulmonary hypoplasia. This body of data suggests that fetal tracheal ligation reverses pulmonary hypoplasia by enhancing normal mechanisms of fetal lung growth, which in turn seems to be dependent on positive ITP/IPP.

Fetal surgery, however, is still faced with significant limitations, mainly with regard to the control of premature labor, and has met with limited success so far. An additional problem associated with human fetal surgery at this time is the fact that the severity and prognosis of pulmonary hypoplasia associated with CDH, for instance, cannot be accurately predicted prenatally, rendering the current indications for fetal surgery in this anomaly dubious. Yet another question to be answered before fetal intervention is indicated is how the lungs that underwent accelerated growth because of tracheal occlusion will function in the mid- to long term. Since bronchial development is complete by 16 weeks gestation, which is long before the time when fetal manipulation is feasible with the technology currently available, those lungs may be so-called "polyalveolar", functioning well at birth, but perhaps not as well, later in life.

In addition, it is known that many other cell types respond to stretch stimulus from increased pressure and/or volume. Tissue or organ hyperplasia in response to increased pressure and/or volume has been observed in the epidermis, the heart, and the digestive and urinary tracts as well.

Accordingly, there exists a need for a therapeutic tool that can actively promote pulmonary as well as other tissue and organ growth, particularly postnatally without the need for fetal intervention.

SUMMARY OF THE INVENTION

The present invention provides a method for facilitating tissue growth in a patient, comprising the steps of providing continuous positive pressure in the tissue in conjunction with administering a fluorocarbon liquid, and maintaining the continuous positive pressure for a period of time effective to facilitate tissue growth in the patient.

In a preferred embodiment, the tissue is lung tissue. The method of the present invention then prefereably further comprises the step of isolating a portion of the lung in the patient, and administering the fluorocarbon liquid to the isolated portion of the lung. The portion of the lung can be isolated using an inflatable cuff. In a preferred embodiment, the method of the present invention comprises the additional step of providing extracorporeal membrane oxygenation while maintaining the continuous positive pressure in the lung.

Preferably, the fluorocarbon is a brominated fluorocarbon, and more preferably, the fluorocarbon is perfluorooctylbromide.

In a preferred embodiment of the present invention, the patient is a neonate less than 2 months of age. Alternatively, the patient can be a fetus, and the method is performed in utero.

The continuous positive pressure is preferably less than 1 to about 20 mm Hg, and is preferably static pressure.

DETAILED DESCRIPTION

Figure 1:
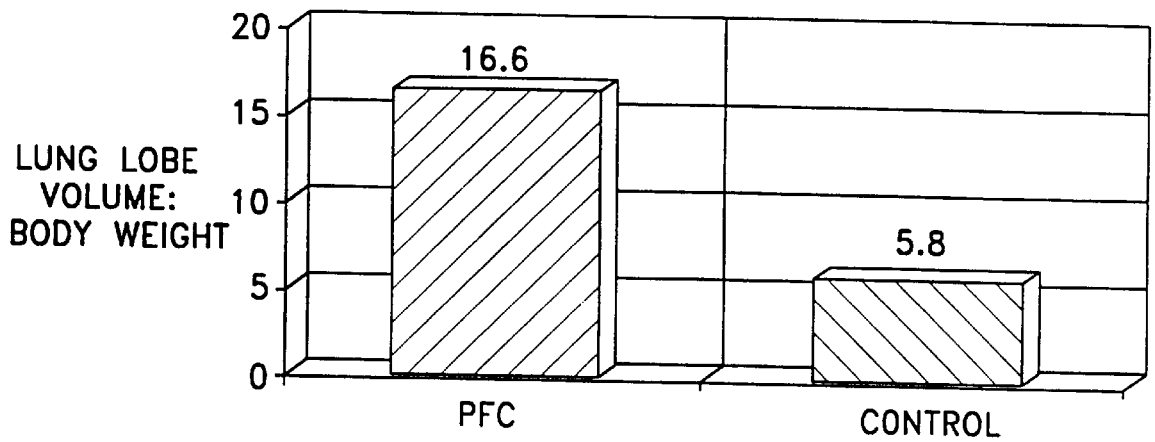
FIG. 1 is a graphic representation of the lung lobe volume to body weight ratio (LV:BW) of animals infused with PFC for three weeks compared with control animals.

The present invention provides for the acceleration of tissue growth by maintaining continuous perfluorocarbon liquid based positive pressure. Fluorocarbon liquid is added to the area surrounding the tissue to create a predetermined pressure in the tissue. This pressure is maintained at a level and for a period of time sufficient to facilitate the accelerated growth and development of the tissue.

It is well known that many cell types respond to mechanical stretch by increasing mitotic activity. Likewise, the phenomenon of tissue or organ hyperplasia in response to stretch from increased pressure and/or volume is common to many organ systems. It is associated, for instance, with epidermal hyperplasia in response to tissue-expander devices; ventricular hypertrophy from systemic or pulmonary hypertension; digestive and urinary smooth muscle hyperplasia proximal to chronic obstructions; and others.

Lung growth can also be controlled by mechanical forces. Modifications of intra-thoracic volume and/or pressure because of pulmonary resections, musculo-skeletal deformities, diaphragmatic disfunction, prosthetic diaphragmatic replacement, or pulmonary collapse, are all known to affect ventilatory mechanics and compensatory lung growth. Nevertheless, the impact of those mechanical forces on lung growth are far from being as pronounced as that observed with the manipulation of fetal airway pressure, as described above. Accordingly, it has been discovered that fluorocarbon liquid-based continuous positive airway pressure is a very powerful stimulus for lung growth in the postnatal period.

A CPAP (continuous positive airway pressure) device alone is not enough to markedly accelerate lung growth; otherwise, ventilatory strategies with high CPAP or high PEEP would also promote pulmonary hyperplasia. If stretch is the ultimate stimulus responsible for growth, then increased airway volume would be more important than increased airway pressure. It is well known that, with the same airway pressure, a lung filled with liquid has a much larger volume than a lung filled with gas. During fetal development, the mammalian lung has its potential airspaces filled with liquid that comes from the pulmonary circulation in response to the osmotic pressure generated by $Cl^-$ secretion of airway and distal lung epithelial cells. During the perinatal period, the pulmonary epithelium changes from a $Cl^-$-secreting to a $Na^+$-absorbing membrane, with consequent reversal of the direction of flow of lung liquid, driving it from the lung lumen back to the pulmonary circulation, preparing the airways to be filled with air.

To determine whether postnatal continuous positive airway pressure with a liquid medium can facilitate lung development postnatally, a liquid fluorocarbon was selected as the pulmonary distending agent because of its minimal absorption by the pulmonary epithelium and minimal toxicity. Furthermore, when infused in the airway, the fluorocarbon liquid is uniformly distributed, rendering both pressure and volume distribution homogeneous.

There are a number of fluorocarbons that are contemplated for medical use. These fluorocarbons include bis(F-alkyl) ethanes such as $C_4F_9CH=CH_4CF_9$ (sometimes designated "F-44E"), i-$C_3F_9CH=CHC_6F_{13}$ ("F-i36E"), and $C_6F_{13}CH=CHC_6F_{13}$ ("F-66E"), cyclic fluorocarbons, such as C10F18 ("F-decalin," "perfluorodecalin" or "FDC"), F-adamantane ("FA"), F-methyladamantane ("FMA"), F-1, 3-dimethyladamantane ("FDMA"), F-di-or F-trimethylbicyclo[3,3,1]nonane ("nonane"); perfluorinated amines, such as F-tripropylamine ("FTPA") and F-tributylamine ("FTBA"), F-4-methyloctahydroquinolizine ("FMOQ"), F-n-methyl-decahydroisoquinoline ("FMIQ"), F-n-methyldecahydroquinoline ("FHQ"), F-n-cyclohexylpurrolidine ("FCHP") and F-2-butyltetrahydrofuran ("FC-75" or "RM101").

Other fluorocarbons include brominated perfluorocarbons, such as 1-bromo-heptadecafluoro-octane ($C_8F_{17}Br$, sometimes designated perfluorooctylbromide or "PFOB"), 1-bromopenta-decafluoroheptane ($C_7F_{15}Br$), and 1-bromotridecafluorohexane ($C_6F_{13}Br$, sometimes known as perfluorohexylbromide or "PFHB"). Other brominated fluorocarbons and fluorocarbons suitable for use in the present invention can be of the type described in U.S. Pat. No. 3,975,512 to Long, which also describes methods of preparing fluorocarbon emulsions. Also contemplated are fluorocarbons having nonfluorine substituents, such as perfluorooctyl chloride, perfluorooctyl hydride, and similar compounds having different numbers of carbon atoms.

Additional fluorocarbons contemplated in accordance with this invention include perfluoroalkylated ethers or polyethers, such as $(CF_3)_2CFO(CF_2CF_2)_2OCF(CF_3)_2$, $(CF_3)_2CFO(CF_2CF_2)_3OCF(CF_3)$, $(CF_3)CFO(CF_2CF_2)F$, $(CF_3)_2CFO(CF_2CF_2)_2F$, $(C_6F_{13})_2O$. Further, fluorocarbon-hydrocarbon compounds, such as, for example compounds having the general formula $C_nF_{2n+1}C_{n'}F_{2n'+1}$, $C_nF_{2n+1}OC_nF_{2n'+1}$, or $C_nF_{2n+1}CF=CHC_nF_{2n'+1}$, where n and n' are the same or different and are from about 1 to about 10 (so long as the compound is a liquid at room temperature) Such compounds, for example, include $C_8F_{17}C_2H_5$ and $C_6F_{13}CH=CHC_6H_{13}$. It will be appreciated that esters, thioethers, and other variously modified mixed fluorocarbon-hydrocarbon compounds are also encompassed within the broad definition of "fluorocarbon" materials suitable for use in the present invention. Mixtures of fluorocarbons are also contemplated. Additional "fluorocarbons" not listed here, but having those properties described in this disclosure, are also contemplated.

It is also contemplated that the method of the present invention be practiced prenatally in utero, in neonates, and in patients suffering from other conditions where new tissue growth would be beneficial, including adult respiratory distress syndrome and major pulmonary resections.

The method of the present invention involves the administration of fluorocarbon liquid to an isolated portion of the body to create continuous positive pressure. In a preferred embodiment, the tissue is the lung. Initially, the lung or portion of lung or other area of isolated tissue is filled with fluorocarbon liquid to a desired pressure. The tissue can be isolated using an inflatable cuff, removable sutures, or other methods well known to those of skill in the art. When the patient's lung is being infused with fluorocarbon liquid, the patient can be oxygenated by providing extracorporeal membrane oxygenation, mechanical ventilation or other means, if desired, according to methods well known in the art. Alternatively, if only a portion of the lung is isolated and infused with fluorocarbon liquid, the remaining lung can be left for normal ventilatory function.

The area of isolated tissue, such as the lung or portion of lung, is filled with fluorocarbon liquid to a desired pressure. The lower limit of suitable pressure is that pressure which is sufficient to facilitate tissue growth. In general, any amount of positive pressure will facilitate tissue growth; preferably, this pressure is about 0.5 mm Hg; more preferably it is 1–3 or 3–6 mm Hg; even more preferably it is 6–8 or 8–10 mm Hg. As an upper limit, the pressure should remain below a level that will damage the tissue. In general, the upper limit of suitable pressure is about 20 mm Hg; more preferably it is about 15 or 12 mm Hg; even more preferably, it is about 10 mm Hg. This positive pressure is maintained for a period of time effective to facilitate tissue growth. The pressure can be static or dynamic during this time period.

The period of time sufficient to facilitate tissue growth is at least 1 hour. Preferably, it is 12, 24, 48, or 72 hours. More preferably, the period of time is 1, 2 or 3 weeks. Even more preferably, the period of time is up to 4 weeks, and longer if desired. The period of time that positive pressure is maintained which is effective in accelerating tissue growth can be determined empirically in each patient, using methods well known to those of skill in the art.

To determine the efficacy of providing postnatal continuous positive airway pressure (CPAP) with a fluorocarbon liquid on lung development, the following experiments were performed. These examples provide information relating to the efficacy of providing CPAP using a fluorocarbon liquid in an experimental sheep model. The general protocol used is described below.

Selection of Experimental Animals

Sheep were chosen for the experiment because of a peculiar anatomical feature that would facilitate the infusion of fluorocarbon liquid into an isolated portion of the lung, leaving the remaining portion of the lung for normal ventilatory function: the bronchus to the so-called right apical lobe branches directly from the trachea in this species. Moreover, the right apical lobe is partially divided by a fissure in a posterior and an anterior-superior portion, with the bronchi to those two portions being easily identifiable, branching from the right apical lobe bronchus. Those anatomical features enabled the isolation of a fairly small portion of the lung for the infusion of fluorocarbon liquid, which in turn enabled the animals to have practically normal life during the course of the experiment.

Animal Preparation

Nine lambs were divided into two groups. Group 1, with four 4-week-old animals, weighing 10.6–11.9 Kg, received general anesthesia with isoflurane in 100% $FiO_2$ and underwent a right lateral thoracotomy. The bronchus to the so-called right apical lobe of the lung, which branches directly from the trachea, was identified. Its first branch, the bronchus to the anterior-superior portion of the right apical lobe (ASRAL), was further dissected and isolated. The parenchyma of the ASRAL, which is naturally partially separated from the posterior portion of the right apical lobe by a fissure, was then completely separated from the rest of the lung with a titanium linear stapler with integral knife (Ethicon, Inc.-Somerville, N.J.). The bronchus to the ASRAL was proximally ligated with no. 5 silk.

After the ASRAL was totally collapsed, its bronchus was opened immediately distal to the ligation site and a pressure-monitoring catheter (Medex, Inc., Hilliard, Ohio), previously exteriorized through a separate stab wound, was introduced and secured in place with no. 2-0 polyester ties. The perfluorocarbon (PFC) perfluorooctylbromide (LIQUIVENT™, Alliance Pharmaceutical Corp., San Diego, Calif.) was then introduced through the catheter, in an amount sufficient to confirm both uniform distribution of the PFC in the ASRAL and no leakage around the catheter through the bronchotomy. A multiperforated tubular chest tube was placed, and the thoracotomy was closed. With the chest tube temporarily closed, the pressure inside the ASRAL was measured with a transducer connected to a digital precision monitor (Hewlett Packard, Waltham, Mass.) and established between 7 and 10 mm Hg.

The animals were then returned to their cages. The chest tube was removed on postoperative day one. The pressure inside the ASRAL was recorded several times a day beginning on postoperative day zero, and maintained between 7 and 10 mm Hg for the following three weeks, by the infusion of more PFC whenever necessary. The animals had no restrictions to ambulate, eat, or drink.

Cefazolin (500 mg IV during the induction of anesthesia and then 500 mg IM every eight hours until postoperative day 3) and Benzatin Penicillin (900,000 U IM every seven days, from postoperative day 3 until postoperative day 21) were administered to each animal. One animal had radiologic follow-up of the chest (facilitated by the fact that PFC is radiopaque) for two weeks.

Group 2 (control), with five animals age- and weight-matched with the animals that were in Group 1 on postoperative day 21, underwent the same operation and pressure monitoring; however, the procedures described below were undertaken not 21 days after the initial surgery, as in Group 1, but immediately after initial instillation of fluorocarbon.

The controls (Group 2) had to be precisely age- and weight-matched with the animals in Group 1 on postoperative day 21 because, in the developing sheep, the lung volume to body weight ratio is not constant; rather, normal growth of lung volume against body weight can be represented by a double-log plot that gives a straight line regression with a slope of 0.67. The controls had also to be submitted to the same operation performed on animals in Group 1 because, to precisely compare lung lobe volume to body weight ratio, the lungs in both groups would have to be preserved by the same method (through native pulmonary vascular bed) and with the same pressure inside the airway (10 mm Hg). The airway pressure was maintained at 10 mm Hg during lung preservation because, if the inflation pressure was increased during lung preservation to 25 cm $H_2O$, as is commonly done, it would have different consequences for each group with regard to lobe volume, since the pleural reaction and adherences resulting from the previous operation in Group 1 would make the pressure-volume curve of the ASRAL in that group different from that of controls, which had no possible restraints to lobe expansion under inflation pressure.

Lung Preparation

The animals from Groups 1 and 2 were weighed and had the pressure inside the ASRAL established at 10 mm Hg (in Group 2, this was done with the chest closed, after no air was coming from the chest tube, which was also temporarily closed). The animals were then anesthetized and submitted to a median sternotomy. The superior and inferior vena cava were isolated. The animals were then heparinized (100 U/Kg IV).

After heparin had been circulating for three minutes, a catheter was introduced into the main pulmonary artery through an opening on the conus arteriosus sealed with a no. 5-0 silk purse-string tie. The superior and inferior vena cava were tied and saline solution was infused through the pulmonary artery at 25 cm $H_2O$ pressure. The left atrium was vented and the left pulmonary artery was clamped. The ventilator was kept with a continuous positive airway pressure (CPAP) of 15 cm $H_2O$ in order to equilibrate pulmonary vascular resistance and facilitate perfusion of the ASRAL. After only saline and no blood was draining from the pulmonary arteries, the saline infusion was discontinued and buffered glutaraldehyde solution was then infused through the pulmonary artery at 25 cm $H_2O$ pressure for approximately two hours. The ASRAL was then completely resected and immersed in a reservoir containing the same buffered glutaraldehyde solution, with the PFC catheter clamped.

At least 24 hours after fixation of the ASRAL, its volume was determined using the method described below. Sampling of fixed tissue was then performed by taking 1–2 $cm^3$ samples from standard positions both in the periphery and in more central areas of the ASRAL. These samples were rinsed in buffer solution and postfixed in 1% osmium tetroxide for two hours. Each specimen was washed, dehydrated, cut into 1 $m^{-6}$ sections, and stained with toluidine blue.

Because there is evidence that during normal postnatal pulmonary growth the immediate subpleural regions grow faster than the more central areas of the lung, care was taken so that sampling of lung tissue was performed by taking fragments from standard positions both in the periphery and in more central sites of the ASRAL.

Morphometric Techniques

Lung lobe volumes were measured by water displacement of the inflation-fixed ASRAL, as previously described by Scherele, *Mikroskopie Bd* 26:57–60 (1970).

Morphometric analysis within the intraacinar region of the lung was performed using a Zeiss laboratory microscope (Zeiss, Germany), with a projection head engraved with a 42-point coherent test lattice, at a magnification of 400× (for a detailed description of this method of analysis, see Weibel, *Stereologic Methods, Vol. I: Practical Methods for Biological Morphometry*, pp 63–236, Academic, San Diego, Calif. (1989) and Weibel and Gomez, *J Appl Physiol* 17:343–348 (1962)). Twenty fields from each lung lobe were studied. An alveolus was defined as an airspace either wholly or partially enclosed by respiratory epithelium, with its remaining boundary formed by an imaginary line connecting the ends of two septae. Alveolar number was estimated by counting alveolar profiles within the test area. Alveolar surface area was estimated by linear intercept. Alveolar numerical density was estimated by the method of Weibel and Gomez, *J Appl Physiol* 17:343–348 (1962).

Statistical Analysis

Statistical analysis was done by analysis of variance (ANOVA) for both groups. The significance of pair-wise comparisons within each group was determined by posthoc testing with the Scheffe-f test at the 95% confidence limit. P values of less than 0.05 were considered significant.

Gross Results

Twenty one days after the initial operation, all animals in Group 1 had the ASRAL significantly increased in size, with some degree of collapse of the posterior portion of the right apical lobe.

EXAMPLE 1

Lung lobe volume. FIG. 1 is a graphic representation of the lung lobe volume to body weight ratio (LV:BW) of animals infused with PFC for three weeks compared with control animals. After three weeks, when normalized to body weight, the mean volume of the ASRAL was markedly increased in animals infused with PFC, with the LV:BW being almost three times as large as that of control Group 2 animals (P=0.0016). The administration of PFC resulted in a significant increase in lung section volume.

EXAMPLE 2

Figure 2:
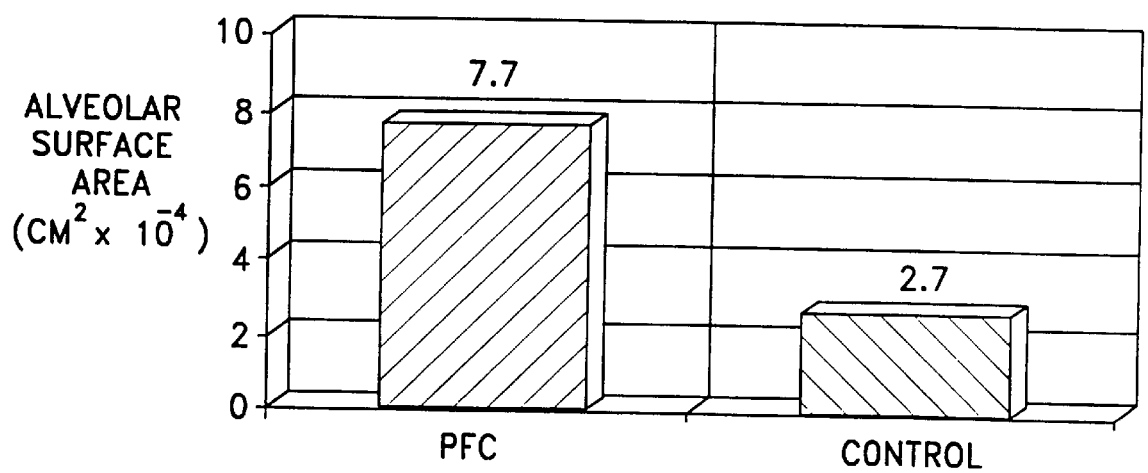
FIG. 2 is a graphic representation of the total alveolar surface area (AlvSA) in animals infused with PFC for three weeks compared with controls.

Alveolar surface area. The ASRAL of the animals in Group 1 had a significantly higher total alveolar surface area (AlvSA), when compared with controls (P=0.0002). FIG. 2 is a graphic representation of these results.

EXAMPLE 3

Figure 3:
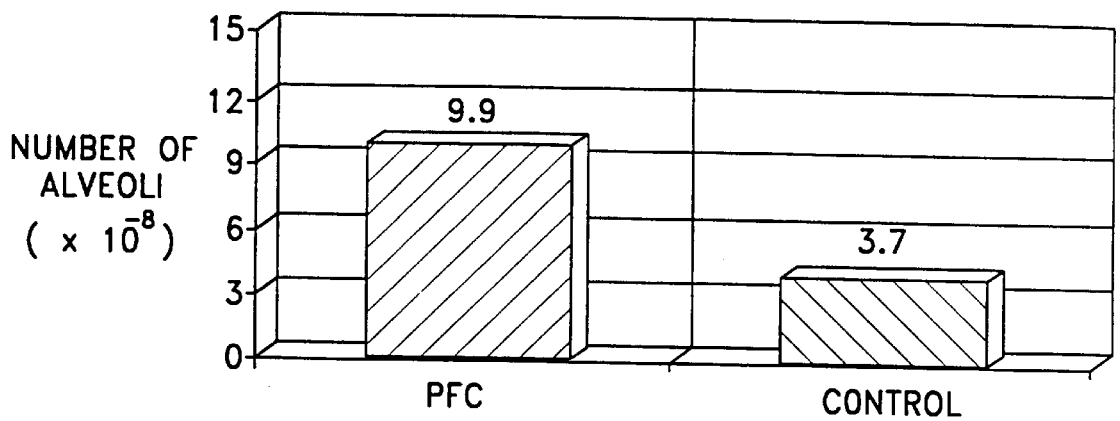
FIG. 3 is a graphic representation of the total alveolar number ($\times 10^8$) in animals receiving PFC for three weeks and in control animals.

Alveolar number. The total alveolar number ($\times 10^8$) in each group of animals is graphically depicted in FIG. 3. The total alveolar number (Alv#) of the ASRAL in the animals of group 1 was almost three times as high as that of controls (P=0.0001).

The data from Examples 1–3 are provided in Table 1, below.

TABLE 1

Morphometric Analysis of Lung Growth

| | Group 1 | Group 2 | P |
|---|---|---|---|
| LV:BW (mL/Kg) | 16.6 +/– | 5.8 +/– | .0016 |
| ALV# ($\times 10^8$) | 9.8 +/– | 3.7 +/– | .0001 |
| AlvSA (cm$^2$ × 10$^{-4}$) | 7.7 +/– | 2.7 +/– | .0002 |

NOTE: Data given as mean +/– standard error of the mean.
Abbreviations: LV:BW, lobe volume to body weight ratio; Alv#, total alveolar number; AlvSA, total alveolar surface area.

EXAMPLE 4

Figure 4:
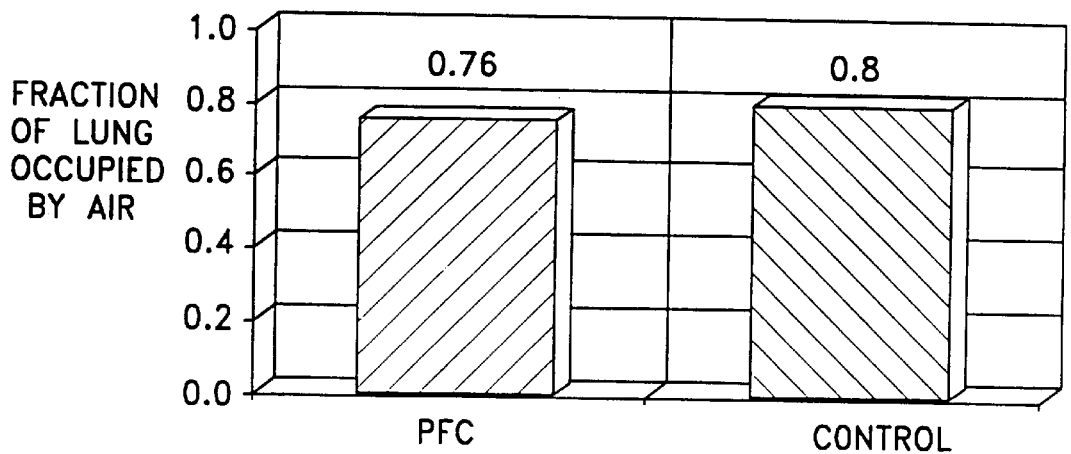
FIG. 4 is a graphic representation of the airspace fraction in animals infused with PFC for three weeks and control animals.

Airspace fraction. FIG. 4 graphically illustrates the airspace fraction in animals infused with PFC for three weeks and control animals. Airspace fraction (ASF), an index of lung maturity, is defined as the percentage of the lung occupied by air. There was no statistically significant difference in ASF when animals in Group 1 were compared with controls in Group 2.

EXAMPLE 5

Alveolar numerical density. Alveolar numerical density (Alv#Dens) is the number of alveoli per cubic centimeter of lung. When analyzed in conjunction with ASF, it is an index of alveolar size. For instance, in pulmonary hypoplasia, both ASF and Alv#Dens are decreased, indicating decreased alveolar size, whereas in pulmonary emphysema, Alv#Dens is also decreased, but ASF is increased, indicating increased alveolar size.

Figure 5:
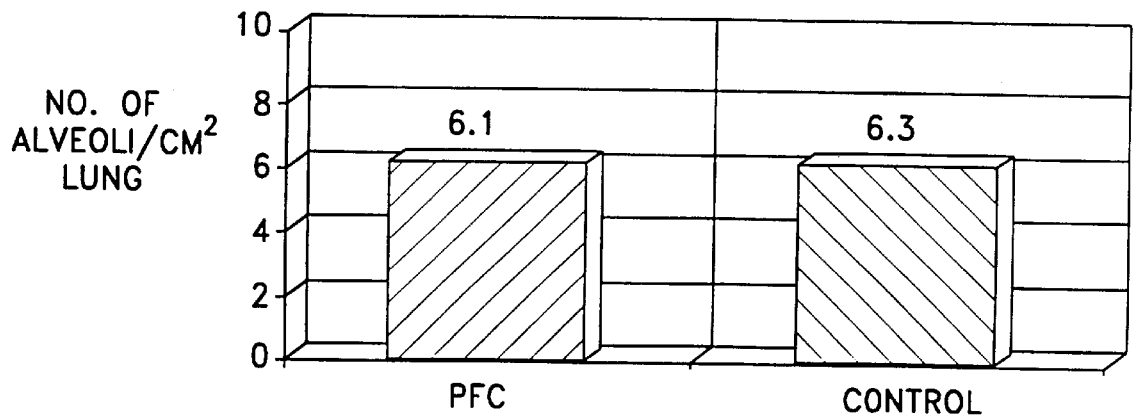
FIG. 5 graphically depicts the alveolar numerical density in animals infused with PFC for three weeks and in control animals.

FIG. 5 graphically depicts the alveolar numerical density in animals infused with PFC for three weeks and in control animals. Animals in Group 1 had statistically the same Alv#Dens as that of controls. This observation, together with the fact that ASF was normal, indicates that animals in Group 1 had normal size alveoli.

The data from Examples 4–5 are provided in Table 2, below.

TABLE 2

Morphometric Analysis of Lung Maturation

| | PFC | Control | P |
|---|---|---|---|
| ASF | 0.76 +/– | 0.8 +/– | NS |
| Alv#Dens | 6.1 +/– | 6.3 +/– | NS |

NOTE: Data given as mean +/– standard error of the mean.

Histology

The ASRAL in Group 1 had microscopic architectural patterns similar to those of controls, with alveoli of normal appearance, thin alveolar septa and no emphysematous changes. However, mild poly- and mononuclear inflammatory infiltrates were found around some conducting airways in Group 1.

Lung weight is also a marker of lung growth. However, even small amounts of PFC, which is very dense, make significant difference when it comes to weight comparisons. Accordingly, ASRAL weight could not be compared between the groups because, although the daily rate of PFC infusion in each animal was recorded, there was almost always some degree of PFC leakage through the stapler line, as the ASRAL grew. The complete removal of PFC, on the other hand, was not feasible.

Conclusion

From the morphometric analysis of LV:BW ratio, AlvSA, Alv #, ASF, and Alv#Dens it was concluded that: (1) postnatal lung growth can be significantly accelerated by continuous intrapulmonary distention with PFC; (2) histologically, lung architecture remains normal, suggesting preservation of the normal maturation process; and (3) prolonged exposure to intrapulmonary PFC (up to at least three weeks) is safe.

A therapeutic tool that can actively promote pulmonary and other tissue growth has been discovered. PFC-based CPAP applied to both lungs during ECMO support provides significant advantages over currently used methods for supportive treatment of neonates with pulmonary hypoplasia. This method of the present invention is much safer than fetal surgery, has a more clear indication, and is relatively simple, and can be combined with technology already well established (ECMO). Moreover, this therapeutic strategy would also eliminate some possibly harmful aspects of the current management of patients with pulmonary hypoplasia, such as intubation and frequent suctioning, which, at least in the fetus and newborn, would be expected to worsen pulmonary hypoplasia.

It has been discovered that the principle of accelerated pulmonary growth through the enhancement of normal mechanisms of lung development is valid not only in utero, but also after birth. As a consequence, the method of the present invention has application not only for the treatment of fetal and neonatal pulmonary hypoplasia, but also for the management of other conditions where new alveolar growth would be beneficial, such as adult respiratory distress syndrome and major pulmonary resections. The method of the present invention has additional application in any condition where facilitation of accelerated tissue growth is desireable.

It should be understood that the embodiments and examples of the present invention, as described, herein, are for purposes of illustration only, and not limitation.

What is claimed is:

1. A method for facilitating tissue growth in a patient, comprising the steps of:

providing continuous positive pressure in said tissue in conjunction with administering a fluorocarbon liquid; and maintaining said continuous positive pressure for a period of time effective to facilitate tissue growth in said patient.

2. The method of claim 1, wherein said tissue is lung tissue.

3. The method of claim 2, further comprising the step of isolating a portion of the lung in said patient, and wherein said fluorocarbon liquid is administered to said isolated portion of said lung.

4. The method of claim 2, further comprising the step of providing extracorporeal membrane oxygenation while maintaining said continuous positive pressure.

5. The method of claim 3, wherein said portion of the lung is isolated using an inflatable cuff.

6. The method of claim 1, wherein said fluorocarbon is a brominated fluorocarbon.

7. The method of claim 6, wherein said fluorocarbon is perfluorooctylbromide.

8. The method of claim 1, wherein said patient is a neonate less than 2 months of age.

9. The method of claim 1, wherein said patient is a fetus, and said method is performed in utero.

10. The method of claim 1, wherein said continuous positive pressure is less than 1 to about 20 mm Hg.

11. The method of claim 1, wherein said continuous positive airway pressure is static.

* * * * *